(12) United States Patent
Reierson et al.

(10) Patent No.: US 9,034,308 B2
(45) Date of Patent: May 19, 2015

(54) ANTI-SENSITIVITY, ANTI-CARIES, ANTI-STAINING, ANTI-PLAQUE ULTRA-MILD ORAL HYGIENE AGENT

(75) Inventors: Robert Lee Reierson, Princeton Junction, NJ (US); Todd William Domke, Newtown, PA (US)

(73) Assignee: RHODIA OPERATIONS, Paris (FR)

( * ) Notice: Subject to any disclaimer, the term of this patent is extended or adjusted under 35 U.S.C. 154(b) by 616 days.

(21) Appl. No.: 12/319,856

(22) Filed: Jan. 13, 2009

(65) Prior Publication Data

US 2009/0123396 A1 May 14, 2009

Related U.S. Application Data

(63) Continuation of application No. 10/783,721, filed on Feb. 20, 2004, now abandoned.

(60) Provisional application No. 60/449,128, filed on Feb. 21, 2003.

(51) Int. Cl.
*A61Q 11/00* (2006.01)
*A61K 8/81* (2006.01)
*A61K 8/55* (2006.01)

(52) U.S. Cl.
CPC .. *A61K 8/55* (2013.01); *A61Q 11/00* (2013.01)

(58) Field of Classification Search
USPC .......................................... 424/70.23, 49, 57
See application file for complete search history.

(56) References Cited

U.S. PATENT DOCUMENTS

| | | | |
|---|---|---|---|
| 4,036,950 A | 7/1977 | Baines et al. | |
| 4,083,955 A | 4/1978 | Grabenstetter et al. | |
| 4,152,421 A | 5/1979 | Tsutsumi et al. | |
| 4,264,580 A | 4/1981 | Barberio | |
| 4,350,680 A | 9/1982 | Harvey et al. | |
| 4,397,837 A | 8/1983 | Raaf et al. | |
| 4,460,565 A * | 7/1984 | Weststrate et al. | 424/52 |
| 4,522,805 A | 6/1985 | Gordon | |
| 4,971,782 A | 11/1990 | Rudy et al. | |
| 4,990,327 A * | 2/1991 | Neirinckx | 424/52 |
| 5,019,373 A * | 5/1991 | Carter et al. | 424/52 |
| 5,180,579 A | 1/1993 | Birtwistle et al. | |
| 5,244,651 A | 9/1993 | Kayane et al. | |
| 5,292,502 A | 3/1994 | Burke et al. | |
| 5,370,865 A | 12/1994 | Yamagishi et al. | |
| 5,374,418 A | 12/1994 | Oshino et al. | |
| 5,550,274 A | 8/1996 | Reierson | |
| 5,554,781 A | 9/1996 | Reierson | |
| 5,603,922 A | 2/1997 | Winston et al. | |
| 5,605,675 A | 2/1997 | Usen et al. | |
| 5,605,676 A | 2/1997 | Gaffar et al. | |
| 5,628,429 A | 5/1997 | Usen et al. | |
| 5,891,233 A | 4/1999 | Salonen et al. | |
| 6,110,445 A | 8/2000 | Gaffar et al. | |
| 6,136,221 A | 10/2000 | Reierson | |
| 6,262,130 B1 | 7/2001 | Derian et al. | |
| 6,416,745 B1 | 7/2002 | Markowitz et al. | |
| 6,464,963 B1 | 10/2002 | Gambogi et al. | |
| 6,685,920 B2 | 2/2004 | Baig et al. | |
| 6,713,049 B1 | 3/2004 | White, Jr. et al. | |
| 6,926,916 B1 | 8/2005 | Day et al. | |
| 7,387,774 B2 | 6/2008 | Faller et al. | |
| 2002/0041852 A1* | 4/2002 | Napolitano et al. | 424/49 |
| 2003/0027742 A1 | 2/2003 | Reierson et al. | |
| 2004/0146466 A1 | 7/2004 | Baig et al. | |
| 2008/0247973 A1 | 10/2008 | Baig et al. | |
| 2010/0316579 A1 | 12/2010 | Fowler et al. | |

FOREIGN PATENT DOCUMENTS

| | | | |
|---|---|---|---|
| GB | 1475251 A | 6/1977 | |
| JP | H05320032 A | 12/1993 | |
| JP | H06-92860 A | 4/1994 | |
| JP | H07-31407 A | 2/1995 | |
| JP | H10298044 A | 11/1998 | |

OTHER PUBLICATIONS

Non-final Office Action of Mar. 13, 2012, for U.S. Appl. No. 12/380,971 to Reierson filed Mar. 5, 2009.
Information Disclosure Statement recieved by USPTO Mar. 22, 2004, with stamped postcard receipt and one page acknowledged by Examiner for U.S. Appl. No. 10/783,721 to Reierson et al, filed Feb. 20, 2004.
Bistey et al, in vitro FT-IR study of the effects of hydrogen peroxide on superficial tooth enamel, Journal of Dentistry, 1048 (2006).
IXPER 60C Calcium Peroxide, Product Data Sheet, Solvay Chemicals, 8-2004.
Caries Res. 1991 (25), 51-57, J. Olsson, A. Carlen and K. Holmberg, Inhibition of Streptococcus mutans Adherence to Hydroxyapatite with Combinations of Alkyl Phosphates and Nonionic Surfactants (1991).

* cited by examiner

*Primary Examiner* — Lezah Roberts

(57) ABSTRACT

This invention relates to a composition useful as a dentifrice comprising a surfactant agent consisting essentially of monoalkyl and dialkyl phosphate esters, wherein the ratio of monoesters to diesters is greater than 1, and optionally an abrasive agent consisting essentially of siliceous materials.

28 Claims, No Drawings

ANTI-SENSITIVITY, ANTI-CARIES, ANTI-STAINING, ANTI-PLAQUE ULTRA-MILD ORAL HYGIENE AGENT

CROSS-REFERENCE TO RELATED APPLICATIONS

This application is a Continuation of U.S. patent application Ser. No. 10/783,721, filed Feb. 20, 2004 now abandoned, which claims the benefit of U.S. Provisional Patent Application Ser. No. 60/449,128, filed Feb. 21, 2003.

FIELD OF THE INVENTION

This application relates to compositions useful in dentifrices and other oral care products. Particularly the invention relates to oral care compositions containing a surfactant agent consisting essentially of water soluble salts of monoalkyl and dialkyl phosphate esters, wherein the molar ratio of monoesters to diesters is greater than 1.

BACKGROUND OF THE INVENTION

The various benefits of using a variety of phosphate esters, as their salts, in oral care formulations have been reported for decades. U.S. Pat. No. 4,152,421 refers to the use of alkali metal or alkanolamine salts of alkyl phosphate esters in dentifrice formulations, citing the high foaming property of the high monoalkyl content phosphate esters (monoalkyl:dialkyl phosphate, or MAP:DAP, weight ratio of 70:30-100:0) as novel, in combination with the "known" property of having no substantial after effects on the tastes and flavors of foods and drinks, especially citrus juices. The concept and range of structures is expanded in a subsequent patent, U.S. Pat. No. 5,370,865, which emphasizes the pleasant taste of basic amino acid salts, specifically with lysine, arginine and histidine. Another early patent, U.S. Pat. No. 4,264,580, covers the incorporation of 0.2-1.0% of an anionic phosphate ester mixture (monoalkyl:dialkyl weight ratios of 1:10 to 10:1) in order to simply reduce the grain formation in a sodium lauryl sulfate-calcium carbonate composition to produce a smooth paste. The next useful property claimed in U.S. Pat. No. 4,350,680 is reduction in the sloughing or desquamation of oral mucosa during tooth brushing action if at least 0.2% of an anionic phosphate ester surface active agent is used as an additional surfactant to sodium lauryl sulfate. U.S. Pat. No. 5,019,373 attempted to improve upon these patents by claiming special advantages for the incorporation of shorter alkyl chain ($C_6$ to $C_9$) dialkyl phosphate esters, particularly dioctyl phosphate. The phosphate ester concentration was rather high, at 2-4 wt. %, in the dentifrice formulation. Evidence for anti-caries activity was offered, which showed a lower rate of calcium demineralization on teeth (in vitro) treated with 1% dioctyl phosphate solution compared to both a 1% sodium lauryl sulfate, which was similar to plain water (placebo), and 1 ppm sodium fluoride (the positive control).

The important subject of remineralization was extensively discussed in a series of patents by Winston and Usen, U.S. Pat. Nos. 5,603,922; 5,605,675; and 5,628,429. Saliva is naturally saturated with calcium and phosphate ions and promotes slow, natural remineralization of carious lesions. The use of supersaturated calcium phosphate solutions or slurries to enhance this natural process was ineffective for a variety of reasons. An effective technique was reported to be the sequential application of concentrated solutions of soluble calcium and phosphate salts to the tooth as disclosed in U.S. Pat. Nos. 4,083,955 and 4,397,837. However, this method was inconvenient and time consuming. In particular, one problem with these techniques is that the remineralization process may stop before the lesion is completely and uniformly remineralized, or "repaired". The rapid remineralization results in a build up of remineralized material on the tooth surface, which then prevents diffusion of the ions into the deeper regions of the lesion, resulting in a void or structure weakening fault in the calcium hydroxyapatite mineral crystal lattice. Furthermore, the solution offered by Winston and Usen was to ultimately develop a two-part toothpaste with water soluble calcium salts in one part and inorganic phosphate salts in the other, along with a two chambered toothpaste tube to deliver it. Prolonged contact of the two salts would result in premature precipitation of the insoluble calcium phosphate salts, which then would not redissolve, hence would be inert as far as the remineralization process is concerned. When the two parts were combined on the tooth brush and promptly introduced into the oral cavity, however, the supersaturated calcium phosphate solution would form in situ and bathe the tooth surface during the brushing process, providing brief periods of replenishment of the ions to enhance the natural process.

More recently, the emphasis has been on the property of the phosphate ester to bond strongly to tooth enamel and dentin and carry other organic components with it. J. Olsson et al. studied the ability of phosphate esters and alkyl ethoxylates to deposit onto hydroxyapatite (HA) in the presence of saliva and inhibit the adherence of *Streptococcus mutans* to the surface. (See Caries Res. 1991, (25), 51, J. Olsson, A. Carlen and K. Holmberg.) By $^{14}C$ labeling experiments, it was determined that 0.20-0.35 mg of the dodecyl-3 EO monoalkyl phosphate (Rhodia counterpart, DERMALCARE® MAP-L-230) bonded to 40 mg HA compared to <0.05 mg of the hexadecyl-8 EO ethoxylate. It was postulated that the phosphate formed a bi-layer, as evidenced by the increased negative charge of the surface. Addition of the ester and ethoxylate together resulted in a decrease in the ester uptake and an increase in the ethoxylate uptake, suggesting that, instead of the second phosphate ester layer, an ethoxylate layer formed on the phosphate layer bound to the HA. An essentially zero surface charge supported this. The phosphate esters alone reduced the deposition of the *S. mutans* but the most dramatic results were obtained when they were used together with the ethoxylate. Olsson's conclusion, namely " . . . the fact that the concomitant incubation of HA, saliva, agents [the ester and ethoxylate], and bacteria seems to increase the effectiveness of the treatment even more than was obtained after pretreatments followed by washings indicates that additional [beneficial] effects may result from exposing the bacteria and salivary components to the surfactants. Indeed, this is . . . particularly relevant if, e.g. treatment is to be performed as a mouth rinsing procedure", is important to commercial applications of phosphate esters in oral care products.

Shortly following this study, Japanese Application No. JP 05-320032 disclosed that dentifrices (mouthwash) containing monoalkyl enriched phosphate ester salt mixtures (e.g. MAP:DAP 90:10 w/w), calcium scavengers (e.g. sodium tripolyphosphate), phenol derivatives and, optionally, water soluble fluorides, formed a film on the surface of the teeth to prevent dental plaque formation and improve acid resistance.

In later filed applications, U.S. Pat. No. 5,605,676 (hereinafter '676 patent) and U.S. Pat. No. 6,110,445 (hereinafter '445 patent), it was disclosed that the uptake and retention of antibacterial agents on dental tissue is substantially increased by incorporation of a phosphate ester surfactant into the formulation. The '676 patent showed that the uptake was inhibited, in a dose response manner, by addition of sodium lauryl sulfate and in the '445 patent disclosed that the anti-bacterial effect is enhanced by use of sodium lauryl sulfate in combination with monolauryl phosphate. The preferred phosphate ester was identified as MAP-20H, manufactured by Kao Corporation (Rhodia counterpart, DERMALCARE® MAP-L-200). Rapid and continued disinfectant action against oral bacteria was also taught for oral care products containing anti-bacterial quaternary ammonium salts of phosphate esters, optionally in combination with the arginine salts, for a pleasant taste in U.S. Pat. No. 5,374,418. It should also be noted that oral care compositions containing phosphate esters and cationic antibacterial agents had been reported decades earlier in GB Patent No. 1,475,251.

Several references citing phosphate ester derivatives were found which were specifically concerned with reduction of hypersensitivity, the subject of this application. The most informative of these was U.S. Pat. No. 5,891,233 (hereinafter '233 patent). The '233 patent discloses a method for reducing pulpal irritation by treating the tooth surface, cavity, or root canal with a bioactive silica containing glass, which releases silica to the surface in a concentration effective to induce crystallization of apatite in the dental tubules and/or on the tooth surface. The '233 patent discloses that a high concentration of calcium and phosphate ions should be maintained in the vicinity of the tubules long enough to allow the ions to diffuse into the tubules as deeply as possible. These concentrations alone, however, are not sufficient. The inventors state "one of the basic features relating to mineralization is that, although serum and tissue fluids [saliva] are supersaturated solutions with regard to calcium and phosphate, spontaneous crystallization does not take place . . . ." As disclosed, to cross the threshold from ion clusters to formation of a crystal nucleus (seed crystal) requires special conditions and/or an outside factor (nucleator). "At least at the beginning of the mineralization process, small membrane lining structures (matrix vesicles) can be seen on the surfaces of the cells forming hard tissue. The vesicles contain calcium binding lipids and alkaline phosphatase." "Since these vesicles only appear at the beginning of the hard tissue formation, it is apparent that there must also be other mechanisms which lead to the mineralization of a tissue. In fact, the extra-cellular matrix contains quite a few organic molecules which may act as nucleators . . . . These molecules include, for example, osteonectin, phosphoproteins, collagen, anionic phospholipids and sulphur containing compounds such as chondroitin sulfate and ceratan sulfate."

U.S. Pat. No. 6,416,745 also emphasizes blocking or plugging up the tubules as the best way to effectively correct hypersensitivity. The patent expands upon the concept by using liposomes (tiny balloons whose walls are lipid bi-layers) to deposit in the tubules and induce mineral [apatite] formation by acting as a mineral template that attracts soluble mineral ions that are naturally present in the dentin tubular fluid and saliva. "These liposome-surface-attracted soluble mineral ions precipitate from the dentin tubule fluid onto the liposome surface, which in turn, acts to nucleate mineral growth in the fluid. The mineral formed in the dentinal tubules will provide a massive, insoluble plug, thereby restoring the tubules to their healthy, naturally impermeable state, blocking tubule fluid movement and insulating the dentinal nerves." Not all liposomes are effective; their surface must be anionic, preferably neutralized as sodium or potassium salts. Liposomes with a choline [amphoteric, e.g. lecithin] or inositol [nonionic, e.g. sugar] surface are not mineral-inducing. Liposomes derived from salts of di(oleoyl)phosphatidic acid (DOPA) are preferred (and the only example given). (Valuable information on liposomes and the sodium salt of DOPA is available on the supplier's web site, www.avantilipids.com.). Numerous other formulation ingredients are suggested such as abrasives, sudsing agents, flavoring agents, humectants, sweeteners, anti-bacterial agents, dyes, etc. Among the sudsing (surfactant) agents, such as sodium lauryl sulfate, alkyl phosphate esters are notably absent. Use of the liposomes in combination with other nerve desensitizing agents such as potassium nitrate, and anti-caries agents such as sodium fluoride, is emphasized in the Claims. The experimental examples are minimal, however, and no clinical testing is provided to back up the Claims.

Another approach, the use of a colloidal form of a polyvalent metal salt, such as zinc or aluminum (among many di- tri- and tetravalent metals claimed) of a polyol (sugar) phosphate ester to plug the tubules was reported in U.S. Pat. No. 5,244,651. Japanese patent, JP 10-298044, discloses the use of insoluble calcium alkyl phosphate salts to similarly plug the dentinal tubules as an effective way to treat hypersensitivity (hyperesthesia). This is, again, only a symptomatic treatment of the problem, not a resolution, as these plugs would inevitably wash out and not be as effective as the present invention.

Additionally, ways to effectively protect teeth from cavities and a variety of other problems by forming a protective, polymeric coating on them were investigated over thirty years ago. Up to that time, no polymeric coating had been found that could be effectively applied to the teeth, in the oral environment, which had the required adhesion, toughness and durability to survive, long term, in the warm, moist oral conditions in the presence of enzymes and under the harsh action of mastication. The use of "temporary" coatings often caused problems of their own. The coating would crack or lift up at its edges, allowing fluids containing bacteria, especially the *Streptococcus mutans*, to penetrate into these narrow fissures, where they could then flourish in a relatively protected area where tooth brush bristles could not dislodge them. Furthermore, it is known that it is not good oral hygiene practice to cut off the tooth surfaces from the active action of the saliva because it contains enzymes, minerals and other beneficial ingredients, calcium and phosphate ions, for instance, which promote slow, natural remineralization of the enamel and dentin surfaces at points of damage, within reason. (The caries develop because the acids released in the metabolism of sucrose by the *S. mutans* destroyed (that is, dissolved) the calcium hydroxyapatite structure more rapidly than this remineralization process could repair it.) It is also believed that the attachment of "unnatural" polymers to tooth structure is not a good idea because it disrupts the calcium hydroxyapatite crystal structure, potentially weakening it. Fluoride treatment, in contrast, was known to be beneficial because the tiny fluoride ion could be incorporated into the hydroxyapatite without seriously disrupting it and actually making it harder and more resistant to acid dissolution (decay). If in excess, however, it may contribute to undesirable discoloration of the tooth surface.

Temporary coatings might be helpful as an effective tooth protective system, however, if they could be conveniently applied by the individual (not requiring a visit to the dental office) and would penetrate effectively into the areas between the teeth, below the gum line and into the fissures (for instance in the top surfaces of molars). They should last from about a half-day to a week and leave no residue behind that would build up or disrupt the natural hydroxyapatite mineral structure. Accordingly, there is a need in the art for improved oral care formulations.

SUMMARY OF THE INVENTION

This invention relates to an oral care composition for reducing hypersensitivity in teeth comprising a surfactant agent consisting essentially of water soluble monoalkyl and dialkyl phosphate esters, wherein the ratio of monoesters to diesters is greater than 1. The invention may also include an abrasive agent consisting essentially of siliceous materials, particularly silica.

The invention further relates to the use of a water soluble, monoalkyl enriched, dodecyl phosphate ester salt surfactant in a dentifrice, particularly a standard toothpaste. It has been discovered that water soluble phosphate ester salts, particularly monoalkyl enriched dodecyl phosphate ester salts, are an effective agent in preventing the pain associated with tooth hypersensitivity.

The invention also relate to a tooth cleaning product comprising a surfactant agent consisting essentially of water soluble salts of monoalkyl and dialkyl phosphate esters, wherein the molar ratio of monoalkyl esters to dialkyl esters is greater than 1, an abrasive agent and optionally a liquid.

The invention also further relates to A tooth powder comprising:
(a) an effective amount of a water soluble monoalkyl dialkyl mixture of phosphate ester salts to reduce tooth sensitivity; and
(b) from about 20% to about 95% by weight of a polishing agent.

The invention provides a mouthwash comprising:
(a) an effective amount of a water soluble mixture of monoalkyl and dialkyl phosphate ester salts to reduce tooth sensitivity;
(b) alcohol;
(c) humectant; and
(d) water.

The invention also provides an oral care composition having anti-sensitivity effect upon teeth which contains an essential anti-sensitivity agent which essentially comprises an effective amount of a water soluble mixture of monoalkyl and dialkyl phosphate ester salts.

Yet another object of the invention is an oral care composition comprising an effective amount of a water soluble alkali metal or a functional amine salt of a phosphate ester, effective to reduce sensitivity in teeth.

Still yet another object of the invention is to provide an oral care composition comprising an effective amount of salts of monoalkyl or monoalkenyl phosphates of Structure (I) and water soluble salts of dialkyl or dialkenyl phosphates of Structure (II):

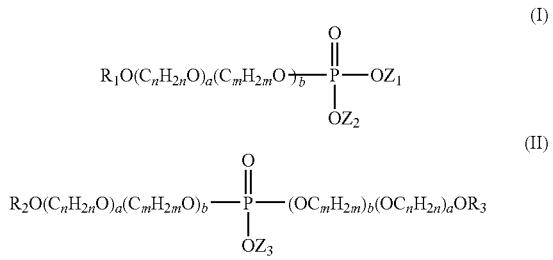

wherein R1, R2 and R3 are from 8 to 22 carbon atoms; n and m are 2 to 4; a and b are 0 to 20; one of Z1 or Z2 is selected from the group consisting of an alkali metal, an ammonium, protonated alkyl amine, protonated alkanolamine, or a protonated basic amino acid; and the other of Z1 or Z2 is selected from the group consisting of hydrogen, an alkali metal, an ammonium, protonated alkyl amine, protonated alkanolamine, or a protonated basic amino acid; and Z3 is selected from a group consisting of an alkali metal, an ammonium, protonated alkyl amine or protonated alkanolamine, or a protonated basic amino acid.

Additionally, the longer term use of a phosphate ester based dentifrice in accordance with the invention has an unexpectedly long lasting, beneficial therapeutic effect.

DETAILED DESCRIPTION OF THE INVENTION

Research on development of anti-barnacle paints for ships' hulls have an interesting analogy to the present invention. In the instance of paints for ships, the use of tributyltin methacrylate as a comonomer provided the twin benefit that, as it hydrolyzed at the surface of the paint coating in contact with the sea water, it released the biocidal tributyltin oxide and increased the water solubility of the coating so it would wash off, a micro-layer at a time. If any of the very tiny barnacle entities had attached to this surface, they would be killed and/or at least rinsed away with it. Food residues, which might attract the barnacles also would be rinsed away. It would seem that this ablation or "self-polishing" action of the coating would be sufficient so that the biocide would be less necessary.

Similarly, a temporary, ablatable coating on tooth surfaces would rinse away any S. mutans that had attached to it. This would serve as an anti-plaque agent by preventing the accumulation of the bacteria and their by-products that form plaque. It may be less necessary to use biocides to kill these bacteria because they would not be able to establish the large colonies on the tooth surfaces to produce acid in sufficient, localized concentration to cause problems. This would preserve the beneficial bacteria. The ablatable, organic coating or film also would provide a protective shield against staining agents (tobacco, tea, etc.) and carry away any which would have adsorbed onto it. Similarly, the coating should serve an anti-calculus function by carrying away the preliminary mineral deposits on it, if any, before they could build up excessively to form calculus or tartar. This approach would be superior to the seemingly vain search for a more permanent coating with the requisite toughness and durability, which would, on one hand, adhere to tooth structure but, on the other, be so slick that nothing would stick to it.

Accordingly, it has been discovered that the water soluble salts of simple, alkyl or alkyl ethoxylate phosphate esters, particularly monoalkyl phosphate esters, would be uniquely suited to the above concept. They have been shown to adhere to and form a hydrophobic coating on calcium salts, tooth enamel and dentin. The advantage over the related alkylphosphonic acids would be that the alkyl phosphate linkage would be hydrolyzed, catalyzed by the phosphatase enzymes in the oral environment, and the hydrophobic, fatty alkyl group would be released from the surface, hence they would function as an ablatable coating with the above stated advantages. This would provide an additional benefit because the now simple, inorganic phosphate group remaining behind, deposited on the tooth, would presumably be retained in its place.

The now "open" anionic site on that phosphate group, exposed to the oral or dentinal fluids, would serve as a "nucleator" to initiate crystal formation and the beginning of mineralization at that location. It would then become an orderly part of the apatite crystal lattice structure in the natural, dynamic remineralization process in combination with the calcium ion rich saliva.

As used herein, an amount of soluble monoalkyl and dialkyl phosphate ester salts that is "effective to reduce tooth sensitivity" means an amount of the phosphate ester salt that provides improved reduction of tooth sensitivity or hypersensitivity, as measured by, for example, clinical tests, as compared to a directly analogous dentifrice or oral hygiene product that does not contain soluble monoalkyl and dialkyl phosphate ester salts in accordance with the invention.

The term "oral care composition" is used to designate products which, in the ordinary course of usage, are retained in the oral cavity for a time sufficient to contact substantially all of the dental surfaces, such as dentifrices, gels, mouthwashes, chewing gums and lozenges, but are not intentionally ingested.

Water soluble salts of monoalkyl phosphate esters useful for the invention include salts monoalkyl or monoalkenyl phosphates of Structure (I) and water soluble salts of dialkyl phosphate esters include salts of dialkyl or dialkenyl phosphates of Structure (II):

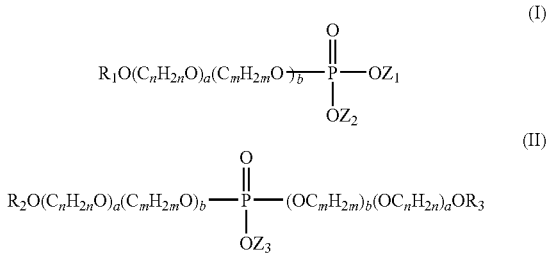

wherein R1, R2 and R3 are, individually, linear or branched, saturated or unsaturated hydrocarbons of from 8 to 22 carbon atoms, n and m are, individually and separately, 2 to 4, and a and b, individually and separately, are 0 to 20. One of Z1 or Z2 is an alkali metal, an ammonium, protonated alkyl amine or protonated functional alkyl amine such as an alkanolamine, including those described in U.S. patent application Ser. No. 10/161,057 and/or a basic amino acid, and the other is hydrogen, an alkali metal, an ammonium, protonated alkyl amine or protonated functional alkyl amine such as an alkanolamine, including those described in U.S. patent application Ser. No. 10/161,057 and/or a basic amino acid. Z3 is an alkali metal, an ammonium, protonated alkyl amine or protonated functional alkyl amine such as an alkanolamine, including those described in U.S. patent application Ser. No. 10/161,057 and/or a basic amino acid.

A composition in accordance with the invention comprises a water soluble monoalkyl and dialkyl phosphate ester salt as the active ingredient or anti-sensitivity agent of an oral hygiene agent. Monoalkyl enriched phosphate esters based on a single alcohol or blend of alcohols, linear or branched, saturated or unsaturated, of from 8 to 22 carbon atoms and degrees of ethoxylation from 0-20, should be effective as anti-sensitivity agents. For foaming and detergency, the C-10 to C-14, 0-4 EO phosphates would be preferred. For formation of a protective coating which retards deposition of S. mutans, longer carbon chain and, optionally, poly(oxyethylene) chain lengths would be useful. Since the esters are generally compatible, the hydrophobe and poly(oxyethylene) chains could be adjusted widely, within the range, to provide phosphate ester components to serve other purposes, such as enhancement of the deposition and retention of actives on the tooth surface, for example, flavor or biocidal ingredients, without significantly interfering with the anti-sensitivity action of the composition. Preferably, the water soluble monoalkyl and dialkyl phosphate ester salts have a molar ratio of monoesters to diesters of at least 1. Preferably the water soluble monoalkyl and dialkyl phosphate ester salt compositions will have molar ratios of the monoalkyl to dialkyl of 70:30, preferably 80:20, and most preferably, 85:15 to 100:00 would be most useful.

Any suitable water soluble monoalkyl or dialkyl phosphate salt may be used, particularly water soluble alkali metal or functional amine salts of phosphate esters. Suitable alkali metal salts include, but are not limited to lithium, sodium and potassium and suitable functional amine salts include, but are not limited to, trialkanolamines and basic amino acids. Other useful water soluble monoalkyl and dialkyl phosphate ester salts are those described in U.S. patent application Ser. No. 10/161,057, now U.S. Pat. No. 6,821,944 to Reierson et al., which is herein incorporated by reference. U.S. patent application Ser. No. 10/161,057, U.S. Pat. No. 6,821,944 to Reierson et al, col. 4, discloses pumpable surfactant compositions of this invention are characterized by a low level of residual phosphoric acid and residual alcohol. Pumpable surfactant compositions of this invention are produced from alkyl phosphate ester compositions high in monoalkyl phosphates relative to dialkyl phosphates, i.e., a molar ratio of mono- to dialkyl phosphate esters of equal to or greater than 60:40, preferably 80:20 or greater and more preferably greater than 90:10. The phosphate ester compositions of low residual phosphoric acid and residual alcohol content and high monoalkyl phosphate content used to produce the pumpable surfactant composition of this invention may be produced by the processes disclosed in U.S. Pat. Nos. 5,463,101, 5,550, 274 and 5,554,781, as well as in EP Patent publication number EP 0 675,076 A2, especially as described in Example 18 of the EP publication. The Example Phosphate A at U.S. Pat. No. 6,821,944 to Reierson et al, col. 6, lines 43-45 has 76.0 wt. % mono(dodecyl) phosphate, 12.4 wt. % di(dodecyl) phosphate, this is a MAP:DAP molar ratio of 90.9:9.1.

A preferred water soluble monoalkyl and dialkyl phosphate ester salt is potassium dodecyl phosphate. The potassium dodecyl phosphate is preferably a monoalkyl enriched surfactant. One particularly useful monoalkyl enriched potassium dodecyl phosphate is commercially available from Rhodia Inc. and sold under the tradename MAP-L-200/K (powder form) or MAP-L-204/K (42% aqueous solution form) in the DERMALCARE® product line.

Any suitable amount of soluble alkyl phosphate ester salts may be used. The amount will vary widely depending on the type of composition desired, for example toothpaste, tooth gel, tooth powder, or mouthwash. Exemplary amounts are provided below with reference to various types of compositions.

In addition to the soluble alkyl phosphate ester salts employed as the anti-sensitivity agent, an oral hygiene composition in accordance with the invention may comprise without intended limitation components customarily used in this field, such as a polishing agent (abrasive agent), sudsing agents, a binder, a humectant, a medicinal agent, a sweetening agent, a flavor and water.

Examples of suitable abrasive agents consisting essentially of siliceous materials, e.g. silica, and examples of other functional additives that may be useful in the compositions of this invention are disclosed in the U.S. Pat. Nos. 6,416,745 and 6,464,963, the disclosures of which are incorporated herein by reference. Compatible and desirable abrasive agent systems may include, hydrated silica, colloidal silica, fumed silica, insoluble sodium metaphosphate, insoluble sodium aluminosilicates, sodium bicarbonate or mixtures thereof. Depending on the form that the oral care composition is to take, the abrasive agent system may be present in an amount up to 70% by weight, preferably 5 to 70% by weight, more preferably from 10 to 60% by weight.

The choice of abrasive agents is dictated by compatibility with the herein described soluble alkyl phosphate ester salts. It will be obvious to one skilled in the art that calcium based abrasive systems, such as calcium pyrophosphate, dibasic calcium phosphates, and calcium carbonate will not be suitable for this invention due to adsorption of the soluble alkyl phosphate ester salts. For example, silica is a preferred abrasive, particularly in conjunction with a potassium dodecyl phosphate, because it retains the excellent foaming characteristics. A first toothpaste formulation was based on dicalcium phosphate dihydrate as the abrasive. The foam volume and quality were found to be inadequate, presumably because of the strong interaction of the potassium dodecyl phosphate (1.2%) with the dicalcium phosphate dihydrate (48.8%). This affinity for and deposition of the potassium dodecyl phosphate onto dicalcium phosphate dihydrate was also observed in earlier experiments in which the ester was evaluated as a method to modify the surface of the particles. The dicalcium phosphate dihydrate particles were notably more hydrophobic after treatment with a solution of the potassium dodecyl phosphate.

Humectants contemplated for use in a composition of the invention include polyols, such as glycerol, sorbitol, polyethylene glycols, propylene glycol, hydrogenated partially hydrolyzed polysaccharides and the like. Exemplary amounts are provided below with reference to various types of compositions.

Optional, but preferred, components which may be included in oral care products in accordance with the invention are organic binders; inorganic thickeners, such as silica; secondary surfactants and/or sweetening agents; coloring agents and/or pigments; anti-microbial agents; and like components conventionally added to toothpastes and gels. Binders suitable for use in a composition of the invention include hydroxyethyl cellulose, and hydroxypropyl cellulose, as well as xanthan gums, Iris moss and gum tragacanth. Binders may be present in the amount from 0.01 to 10%. Sweeteners suitable for use, e.g. saccharin, may be present at levels of about 0.1% to 5%.

Anti-caries agents may also be used in conjunction with the oral anti-sensitivity agent in accordance with the invention. For example oral hygiene compositions in accordance with the invention may include those commonly used in oral health care compositions, such as sodium fluoride, stannous fluoride, sodium monofluorophosphate, zinc ammonium fluoride, tin ammonium fluoride, calcium fluoride and cobalt ammonium fluoride and the like. Preferred compositions in accordance with the present invention will include a fluoride source. Fluoride ions are typically provided at a level up to 1500 ppm, preferably 50 to 1500 ppm, although higher levels up to about 3000 ppm may be used as well.

Compositions in accordance with the present invention may also include antibacterial agents. Suitable antibacterial agents include, phenolics and salicylamides. Such antibacterial agents, in addition to other functional agents, including therapeutic agents and nutrients, may be incorporated into the liposomes themselves in accordance with the present invention.

Dyes/colorants suitable for oral health care compositions, i.e. FD & C Blue #1, FD & C Yellow #10, FD & C Red #40, etc., may be included as well. Various other optional ingredients may also be included in the compositions of the invention such as preservatives; vitamins, for example, vitamins C and E; and other anti-plaque agents, for example, stannous salts, copper salts, strontium salts and magnesium salts. Compositions may also include anti-calculus agents such as a water-soluble alkali metal salt of a polyphosphate, buffering agents such as alkali metal orthophosphates, phosphoric acid, alkali metal glycerophosphates, tartrates, or citrates, other anti-caries agents, for example, calcium glycerophosphate, sodium trimetaphosphate; anti-staining compounds, for example silicone polymers; plant extracts; and mixtures thereof. Additionally, polymers, particularly anionic polymers, such as polycarboxylates or polysulfonates, or polymers containing both a carboxylate and a sulfonate moiety, phosphonate polymers or polyphosphates may be used.

A toothpaste or gel in accordance with the invention will generally comprise a surfactant agent consisting essentially of water soluble salts of monoalkyl and dialkyl phosphate esters, wherein the molar ratio of monoesters to diesters is greater than 1, a compatible abrasive agent system, and a liquid in an amount to provide the desired consistency.

In a toothpaste, the liquid may include water, humectant and binder, generally, in an amount ranging from about 10 to about 90% by weight of the toothpaste. Water is a desirable component when a toothpaste or gel is being prepared. Water comprises up to about 50%, and preferably about 5-35% by weight of the toothpaste. However, an anhydrous toothpaste or gel can be formulated if desired.

A humectant is also a desirable component in a toothpaste or gel. Preferably, the humectant comprises about 5% to about 85% by weight of the formulation, and preferably from about 10% to about 70% by weight of the formulation. In translucent gels, where the refractive index is an important consideration, it is preferred to use higher ratios of humectant to water than in opaque pastes. For a gel the ratio of humectant to water should preferably be above about 0.5 to 1, and more preferably above 1 to 1.

A tooth powder in accordance with the invention may comprise a polishing agent which is compatible with the soluble monoalkyl and dialkyl phosphate ester salts described herein, such as sodium bicarbonate or hydrated silica. Generally, the polishing agent will be in an amount from about 20 to about 95%, and preferably above 50% by weight of the formulation. An effective amount of the monoalkyl and dialkyl phosphate esters as described herein is typically from about 0.1 to about 10% and preferably about 1% to about 5% by weight of the tooth powder formulation. Optional, but preferred, components which may be included in the toothpowder are a flavoring agent and/or sweetening agent, an anti-calculus agent such as a water-soluble alkali metal salt of a polyphosphate, an anti-caries agent such as sodium fluoride or sodium monofluorophosphate, buffering agents such as alkali metal orthophosphates, phosphoric acid, alkali metal glycerophosphates, tartrates, or citrates, and one or more processing aids such as a flow aid to insure product uniformity.

A mouthwash in accordance with the invention generally comprises alcohol, water, humectant, and an effective amount of the monoalkyl and dialkyl phosphate ester salts as described herein. An effective amount of the monoalkyl and dialkyl phosphate ester salts in the mouthwash is typically from about 0.1% to about 10% and preferably from about 1% to about 5% by weight of the mouthwash. Optional, but preferred, components which are included in the mouthwash are a flavoring agent and/or sweetening agent, an anti-calculus agent such as a water-soluble alkali metal salt of a polyphosphate, an anti-caries agent such as sodium fluoride or sodium monofluorophosphate, buffering agents such as alkali metal orthophosphates, phosphoric acid, alkali metal glycerophosphates, tartrates, or citrates.

The water soluble monoalkyl and dialkyl phosphate ester salt of the invention may be prepared by any suitable method. For example, the potassium dodecyl phosphate, MAP-L-200/

K, was prepared by methods described in U.S. Pat. Nos. 5,550,274; 5,554,781; 6,136,221; and 6,262,130, the disclosures of which are incorporated herein by reference. A 42% aqueous solution, of for example, DERMALCARE® MAP-L-204/K, may be spray dried by standard techniques at 200° C. The $^{31}$P and $^{13}$O NMR spectra indicate that the spray drying process has little effect upon the composition except that the residual phosphoric acid is partially converted to pyrophosphoric acid (potassium salt) and the residual dodecanol is removed. The highest MAP:DAP molar ratio of U.S. Pat. No. 5,554,781 Table 1, is that of Example 5 which discloses Phosphoric acid:MAP:DAP of 0.142:0.787:0.072 which if normalized for only MAP:DAP is 0.916:0.084.

As part of a comprehensive oral care program, it would be desirable to combine a composition containing the soluble phosphate ester salt anti-sensitivity agent, for example a soluble phosphate ester salt anti-sensitivity agent containing toothpaste, with other oral care products, such as mouth wash, chewing gum, soluble oral care strips (similar to the LISTERINE® oral care strips) and even lozenges, all of which would beneficially contain the soluble phosphate ester salt anti-sensitivity agent and, optionally, an appropriate ethoxylate agent (e.g. the hexadecyl-8 EO ethoxylate) for replenishment of the S. mutans repelling coating between brushings. Addition of an anti-bacterial agent might be helpful but, perhaps not required at the level typical in non-phosphate ester salt products. The phosphate esters and linear fatty alcohols on which they are preferably based, are natural and safe for ingestion in the minor amounts incidental to their use in oral care products.

It should be noted that it is important that the natural remineralization process be controlled and gradual. As previously discussed, if remineralization proceeds too rapidly, a build up at the top surface may occur, preventing diffusion of the minerals into the deeper core of the lesion or tubule, hence creating an undesirable void or defect in the calcium hydroxyapatite structure beneath the thin surface layer, as suggested by U.S. Pat. No. 5,603,922. For the same reason, entrapment of "foreign" organic components in the tooth structure, such as the insoluble calcium or other polyvalent metal salts or vesicles should be avoided. Phosphonate surfactants or polymers also would be subject to this entrapment, because the phosphorus-carbon bond in the alkyl phosphonate would not be subject to hydrolysis.

These attributes would have special importance in the case of dental hypersensitivity. Dental hypersensitivity generally results from exposure of the tubules in dentin to oral fluids and temperature changes. As the general population ages and the individual's teeth become worn from frequent brushing, gums recede or pockets develop from poor oral hygiene habits. The problem of dental hypersensitivity is increasing as evidenced by the number of brands of anti-sensitivity toothpastes on the store shelves has quadrupled in the past five years. Currently, the most common treatment is to use a toothpaste containing 5% potassium nitrate. The potassium and nitrate ions diffuse into the tubules to desensitize the nerves, hence reducing the pain, but do not correct the source of the problem. This treatment of the symptoms does nothing to correct or heal the condition causing the pain. Besides the cost to the consumer of up to four times the price of a comparable "non-sensitivity" formulation, these saltpeter formulations also uniformly carry a warning on their labels that they should not be used for more than four weeks without the approval of a dentist.

Again, it is believed that the soluble salts of simple phosphate esters are well adapted to resolve this problem. Since the water soluble phosphate ester salts typically are very effective surfactants (low surface tension and critical micelle concentration) and cleansing agents (proven for skin and claimed in dentifrice formulations), they would effectively penetrate deeply into the tiniest crevices and tubules, where the phosphate head group would anchor to the calcium hydroxyapatite tooth structure. The hydrophobic tail of the water soluble salts would provide temporary relief by partially blocking the tubule and reducing the rate of fluid exchange, which contributes to the irritation. As the phosphate ester link is hydrolyzed, the phosphate head group would remain on the tooth, where it is subsequently fixed in place by reaction with calcium in the saliva as the fatty alcohol "tail" is washed away.

Additionally, the longer term use of the phosphate ester-based toothpaste has demonstrated an unexpectedly long lasting, beneficial therapeutic effect. In the case of the commercially available saltpeter formulations (e.g. in SENSODYNE® toothpaste), the sensitivity normally would return within two to three weeks after they were discontinued, consistent with the action of the potassium nitrate as a temporary, nerve desensitizing agent. In contrast, continuing freedom from pain associated with the hypersensitivity condition was experienced for fifteen months after the completion of the evaluation period for a toothpaste in accordance with the invention. This long term relief can be explained by and is evidence of the "healing" mineralization process that presumably occurred in the tubules over the twenty-one week period of use. The long lasting effectiveness suggests that the deposit resulting from treatment with the water soluble phosphate ester salt it is more difficult to abrade or brush away because it is, at least, in a protected position, deep in the tubules and likely a part of the more permanent, remineralized surface of the tooth structure, which had closed the tubule opening.

Yet another benefit of the use of phosphates as the principal detergent surfactant in the toothpaste is the result of its very low irritancy potential and tissue compatibility. It has been reported to substantially reduce the stripping of oral mucosa through sloughing or desquamation compared to sodium lauryl sulfate, the most commonly used toothpaste surfactant. The detersive and foaming properties of the comparable monoalkyl phosphate ester, potassium lauryl phosphate, has been shown in lab and skin cleanser tests to be at least equivalent to the sodium lauryl sulfate. Related to the harshness of the sodium lauryl sulfate is the retardation of the healing process of canker sores and other oral mucosa lesions. In contrast, phosphate esters, particularly monoalkyl phosphate esters, have been shown to have the lowest skin irritation potential of any anionic (or cationic) surfactant. In the absence of such daily irritation, it is reasonable to expect that such lesions would not become so painfully large and would heal more quickly.

The substance and compatibility of phosphate esters to tissues, especially skin, has been utilized to increase the deposition of active ingredients onto and into them. For instance, a system to enhance the delivery of pain relieving and anti-inflammatory active ingredients, methyl salicylate, menthol and camphor, to joints and muscles is based on phosphate esters. In toothpaste applications, enhanced uptake and retention of antibacterial agents, such as Triclosan, onto dental "tissue" (teeth) has been reported. It stands to reason, then, that phosphate esters would deposit other organic therapeutic, flavor or fragrant "freshening" ingredients in the oral cavity for a longer acting, more effective therapeutic activity or feeling of freshness and cleanness.

In this regard, the stability to oxidation would provide yet another benefit. The phosphate esters of simple, linear aliphatic alcohols contain no "active", covalently bound hydrogens, which would be subject to peroxide oxidation. Hence the peroxides used in tooth whitening formulations would not be decomposed by them and the film they form on the tooth would retain a higher concentration of the peroxide (especially, but not limited to, basic oxidants such as urea or carbamide peroxides) in contact with the tooth surface for a longer period of time (hours), until the phosphatase harmlessly hydrolyzes the ester link and the film and the peroxide oxidation product residues are washed cleanly and completely away. The remineralization process promoted by the phosphate group left behind on the dental surface may serve to partially compensate for the damage to the tooth structure potentially caused by the action of the peroxide.

In summary, the advantages of the oral hygiene compositions of the invention include: providing an ablatable coating for anti-adherence of stain and bacteria to teeth; desensitization of teeth having dentinal hypersensitivity; low irritancy and improved tissue compatibility or tolerance; increased deposition of various ingredients, including anti-microbials, flavor oils; compatibility with peroxide whitening agents; and anti-tartar characteristics. In order to further illustrate the invention and the advantages thereof, the following non-limiting examples are given.

EXAMPLES

Example 1

For the initial evaluation, a test subject was chosen, who, because of poor dental hygiene habits as a child, had developed periodontal problems. Prior treatment of the condition included elimination of undesirably deep pockets between the gums and molars by surgical removal of gum tissue, exposing dentin normally below the gum line. With advancing age, these areas had become increasingly sensitive to temperature changes and some fluids. The use of the saltpeter toothpaste formulations had become a standard practice; switching to conventional, "non-sensitive" formulations for more than two weeks consistently resulted in pain that required return to the saltpeter formulations, in spite of their label warnings.

The subject began the test period using a test formulation. The test formulation was prepared using potassium dodecyl phosphate, MAP-L-200/K, which is commercially available from Rhodia Inc. in the DERMALCARE® phosphate ester line. The test formulation was prepared by methods described in the examples below. A 42% aqueous solution, DERMALCARE® MAP-L-204/K, (from Examples 1 and 2) was spray dried by standard techniques at 200° C. in a pilot plant unit. The $^{31}$P and $^{13}$C NMR spectra indicated that the spray drying process had little effect upon the composition except that the residual phosphoric acid was partially converted to pyrophosphoric acid (potassium salt) and the residual dodecanol was removed.

The subject used the test formulation in his daily, morning tooth brushing regimen with a soft bristle brush provided by his dentist, with use of no additional oral care products except for dental floss. The brushing procedure was to squeeze about 4 g of the paste over the top of the moistened brush bristles, then spread the paste uniformly over the tooth surfaces with a circular brushing motion. The buccal and lingual surfaces were then brushed with a vertical motion, away from the gums, and the molar crowns were brushed with a side-to-side motion. The excess foam was expelled. This was followed by a scrubbing motion in which the bristles gently massaged the gums and were forced into the areas between the teeth and at the gum line, especially in the left, lower molar area, where there were 5 mm pockets. This sequence required about four minutes, after which the mouth was rinsed with a few ounces of fresh water. Flossing, especially in the areas with deep periodontal pockets, followed on a three times per week basis.

At no time during the evaluation period were hypersensitivity problems experienced. Additionally, this testing program affirmed the earlier reports and claims of the outstanding detersive and cleansing action of the soluble phosphate ester as the sole surfactant component (teeth were as clean and smooth as they would be after a cleaning and polishing procedure administered by a dentist or oral hygienist), the lack of effect on the taste of beverages such as orange juice or milk, consumed after its use, and the very low tissue irritation potential. As evidence of the cleaning and polishing effectiveness, occasionally a squeaking sound ("squeaky clean") could be heard during the brushing process.

As a result of the exceptionally low irritation potential, the incidence and severity of canker sores were markedly reduced over the extended period of evaluation. Those which appeared during the first month did not grow to the "normal" size and healed more quickly. Atypically, none appeared during the second month even though the test subject accidentally bit his left buccal surface once, during mastication, leaving a region of raw, injured tissue. Normally, this damaged, exposed area would have been more readily attacked by germs always present in the oral cavity, resulting in a sore within a few days. The only deficiency noted was the slightly lower foam level of the toothpaste compared to that of the standard, commercial products. This was regarded as inconsequential compared to the above benefits provided by this first prototype and likely could be corrected in subsequent formulations.

The subject visited his dentist for his regular, 6 month check-up during the eighteenth week of the test. No problems were noticed; no cavities, the periodontal pocket depth was stable in the problem areas and all fillings were intact. The amount of tartar removed was normal, about the same as always. The last brushing of the study was completed after twenty-one weeks, coinciding with the end of the test formulation toothpaste supply.

Rather than return directly to the use of the saltpeter toothpastes, the subject then switched to regular toothpaste, with "Tartar Protection" and fluoride, to determine how long it would be until the hypersensitivity problem returned. Surprisingly, instead of the usual two or three week period, the subject experienced no significant hypersensitivity problems during the twelve weeks that lapsed from the end of the test period to near the filing date of the provisional patent application. This hypersensitivity symptom free condition has continued to persist during the subsequent twelve month period to the date of this application preparation. Unfortunately, the higher frequency, longevity and degree of irritation of the canker sores did return to "normal" within a month of the end of the test period.

The coating effect seemed to last for about a "working day" (8-12 hours). Overnight, especially, the typical film of oral "refuse" tended to accumulate on the teeth, particularly at the gum line. This film was easily removed by brushing the next morning. As documented in references cited in this application, optionally, the protection afforded by the phosphate ester protective film could be achieved or prolonged by use of a mouth wash, soluble oral care strip, chewing gum or lozenge, all of which would beneficially contain the water soluble phosphate ester salt and, optionally, an appropriate nonionic surfactant (e.g. hexadecyl-8 EO ethoxylate). In these additional product options, greater latitude would be allowed in the use of other additives or components and in selection of the phosphate ester salts, with respect to hydrocarbon chain length and structure, degree of ethoxylation and counter (neutralizing) ion, for film characteristics because the foam production property would not be as important as in toothpastes or gels.

It is believed the mechanisms described above are, at least in part, responsible for the remarkable effectiveness of this potassium dodecyl phosphate based formulation as an anti-sensitivity oral care product and provides a basis for its long delay of recurrence of the hypersensitivity pain (by correction of the cause).

Example 2

Preparation of Potassium Dodecyl Phosphate

The potassium dodecyl phosphate, MAP-L-200/K, was prepared by methods described in U.S. Pat. Nos. 5,550,274; 5,554,781; 6,136,221; and 6,262,130, the disclosures of which are incorporated herein by reference. The 42% aqueous solution, DERMALCARE® MAP-L-204/K, was spray dried by standard techniques at 200° C. in a pilot plant unit. The $^{31}P$ and $^{13}C$ NMR spectra indicated that the spray drying process had little effect upon the composition except that the residual phosphoric acid was partially converted to pyrophosphoric acid (potassium salt) and the residual dodecanol was removed.

Interaction with Calcium Phosphates

Addition of 1 Kg of dibasic calcium phosphate, dihydrate powder to 1800 ml of a 10% solution of potassium dodecyl phosphate (pH ~7) significantly reduced the foaming of the solution and rendered the calcium phosphate abrasive hydrophobic. Disappearance of foaming was indicative of loss of surfactant from bulk solution. Increased hydrophobicity of the calcium phosphate was indicative of surfactant adsorption onto the solid particles.

A typical calcium based abrasive tooth paste formulation was prepared using dibasic calcium phosphate, dihydrate as the abrasive and conventional mixing techniques as shown below. Upon dilution of this formulation (3:1, w/v) the foam volume and quality were found to be significantly reduced in comparison to a silica abrasive based formulation. This finding was in contrast to an earlier patent discussed above (U.S. Pat. No. 4,152,421) and was presumably so because of the strong interaction of the potassium dodecyl phosphate (1.2%) with the calcium phosphate abrasive.

|  | Wt % |
|---|---|
| Distilled Water | 24.940 |
| Sodium Monofluorophosphate | 0.760 |
| Tetrasodium pyrophosphate | 0.250 |
| Cellulose Gum (CMC 7MXF) | 1.000 |
| Glycerin (99.7% USP) | 22.000 |
| Victor DF[1] | 48.760 |
| Flavor Oil | 0.890 |
| Sodium Saccharin | 0.200 |
| DERMALCARE ® MAP-L-200/K[2] | 1.200 |
| Total | 100.000 |

[1]Dibasic calcium phosphate, dihydrate,
[2]Spray dried powder of potassium dodecyl phosphate.

Examples 3 to 7

Representative Toothpaste and Gel Formulations

The toothpastes and gels made herein were made using conventional mixing techniques and used in a conventional manner. The following examples further illustrate the invention, but it is understood that the invention is not limited thereto. All amounts and proportions referred to herein and in the appended Claims are by weight and temperatures in degrees Celsius unless otherwise indicated.

|  | 3 | 4 | 5 | 6 | 7 |
|---|---|---|---|---|---|
| Distilled Water | 9.802 | 10.340 | 5.000 | 11.89 | 5.279 |
| Sodium Fluoride | 0.220 | — | 0.243 | — | 0.243 |
| Sodium Monofluorophosphate | — | 0.760 | — | 0.760 | — |
| Tetrasodium pyrophosphate | — | — | — | 3.500 | 2.000 |
| Cellulose Gum (CMC 7MXF) | 0.400 | 0.400 | 0.400 | 0.400 | 0.600 |
| Sorbitol (70% soln.) | 61.633 | 60.000 | 36.607 | 50.000 | 40.100 |
| PEG 600 | 3.000 | 3.000 | — | 3.000 | — |
| Glycerin (99.7% USP) | — | — | 5.000 | 5.000 | 5.000 |
| Sodium Bicarbonate | — | — | 50.000 | — | 43.728 |
| TIXOSIL 73[1] | 18.000 | 18.000 | — | 18.000 | — |
| TIXOSIL 43[2] | 4.500 | 4.500 | — | 4.500 | — |
| Flavor Oil | 0.685 | 0.800 | 1.000 | 1.000 | 0.950 |
| Sodium Saccharin | 0.300 | 0.300 | 0.300 | 0.300 | 0.650 |
| FD&C Blue No. 1 (1% soln.) | 0.200 | 0.200 | 0.200 | 0.200 | 0.200 |
| Titanium Dioxide | — | 0.200 | — | 0.200 | — |
| DERMALCARE ® MAP-L-200/K[3] | 1.260 | 1.500 | 1.250 | 1.250 | 1.250 |
| Total | 100.000 | 100.000 | 100.000 | 100.000 | 100.000 |

[1]Hydrated silica abrasive,
[2]Hydrated silica thickener,
[3]Spray dried powder of potassium dodecyl phosphate.

Examples 7 to 11

Representative Toothpowder Formulations

The toothpowders made herein were made using conventional mixing techniques and used in a conventional manner. The following examples further illustrate the invention, but it is understood that the invention is not limited thereto. All amounts and proportions referred to herein and in the appended Claims are by weight and temperatures in degrees Celsius unless otherwise indicated.

|  | 7 | 8 | 9 | 10 | 11 |
|---|---|---|---|---|---|
| Sodium Bicarbonate | 97.757 | 96.74 | 91.507 | 91.240 | 89.390 |
| Zinc Oxide | — | — | 2.000 | 2.000 | 2.000 |
| Sodium Fluoride | 0.243 | — | 0.243 | — | — |
| Sodium Monofluorphosphate | — | 0.760 | — | 0.760 | 0.760 |
| Tetrasodium pyrophosphate | — | — | 3.500 | 3.500 | 5.350 |
| Flavor Oil | 1.000 | 1.000 | 1.000 | 1.000 | 1.000 |
| Sodium Saccharin | 0.500 | 0.500 | 0.500 | 0.500 | 0.500 |
| DERMALCARE ® MAP-L-200/K[1] | 0.500 | 1.000 | 1.250 | 1.000 | 1.000 |
| Total | 100.000 | 100.000 | 100.000 | 100.000 | 100.000 |

[1]Spray dried powder of potassium dodecyl phosphate.

Examples 12 to 14

Representative Mouthwash Formulations

The mouthwash/rinse formulations made herein were made using conventional mixing techniques and used in a conventional manner. The following examples further illustrate the invention, but it is understood that the invention is not limited thereto. All amounts and proportions referred to herein and in the appended Claims are by weight and temperatures in degrees Celsius unless otherwise indicated.

|  | 12 | 13 | 14 |
|---|---|---|---|
| Glycerin (99.7% USP) | 50.000 | 50.000 | 60.000 |
| Ethanol (200 PF) | 2.000 | 2.000 | 2.000 |
| Sodium Fluoride | — | 0.05 | — |
| Tetrasodium pyrophosphate | — | — | 2.000 |
| Flavor Oil | 0.25 | 0.25 | 0.25 |
| FD&C Blue #1 | 0.00025 | 0.00025 | 0.00025 |
| D&C Yellow #10 | 0.00060 | 0.00060 | 0.00060 |
| DERMALCARE ® MAP-L-200/K[1] | 0.500 | 1.000 | 1.250 |
| Water | q.s. to 100 | q.s. to 100 | q.s. to 100 |
| Total | 100.000 | 100.000 | 100.000 |

[1]Spray dried powder of potassium dodecyl phosphate.

Example 15

Preparation of Toothpaste Formulation

The ingredients listed in Table 1 were combined in the indicated percentages, by weight, in 1800 g batches, following the procedure described.

TABLE 1

Test Formulation Composition and Preparation Procedure

| INGREDIENT | Wt., % |
|---|---|
| Distilled Water | 9.802 |
| NaF | 0.220 |
| Sodium Saccharin | 0.300 |
| PEG 600 (PEG 12) | 3.000 |
| Cellulose Gum (CMC 7MXF) | 0.400 |
| Sorbitol (70% soln.) | 61.633 |
| FD&C Blue No. 1 (1% soln.) | 0.200 |
| TIXOSIL 73 | 18.000 |
| TIXOSIL 43 | 4.500 |
| CMS Generic 3055 Flavor | 0.685 |
| MAP* | 1.260 |
| Total | 100.000 |

*DERMALCARE ® MAP-L-200/K powder was prepared by spray drying of DERMALCARE ® MAP-L-204/K, a 42% solids aqueous solution of potassium dodecyl phosphate.

Procedure:

1. Heat polyethylene glycol (PEG 600), Water & Sorbitol to 49° C.
2. Dissolve sodium fluoride (NaF) and Sodium Saccharin into Distilled Water.
3. Separately disperse carboxymethylcellulose (CMC 7MXF) into the PEG 600. Mix 10 minutes.
4. Weigh 70% solution of sorbitol into a plastic, 2 L beaker.
5. Add CMC/PEG dispersion to Sorbitol and mix 10 minutes.
6. Add NaF/Sodium Saccharin solution and FD&C Blue No. 1 to the Sorbitol. Mix 10 minutes.
7. Blend in the potassium monoalkyl phosphate powder (MAP); continue to mix 20 more minutes.
8. Transfer this mucilage to the Ross mixer, then add silica (TIXOSIL 73 brand and TIXOSIL 43 brand from Rhodia Inc.).
9. Hand mix silica until silica is wetted out, then Ross mix for 5 minutes.
10. Stop and scrape down sides and blades of Ross mixer.
11. Close mixer and mix under vacuum. During this process, while pulling the vacuum, use the ball valve to gradually reduce the pressure by stopping at 20, 25 and 27 in. Hg vacuum for one min. at each point.
12. Finally, leave ball valve open. When the vacuum stabilizes at 27 in. Hg or better, start the timer and mix an additional 15 minutes.
13. Stop mixer, release vacuum, add the 3055 Flavor.
14. Reapply vacuum and mix for an additional 5 minutes.
15. Release vacuum and transfer paste to tubes and seal.

Toothpaste Stability Evaluation

Two important stability criteria must be met by the final toothpaste formulation for it to be considered for commercial use.

One is viscosity build. Here, there are two important benchmarks. The first is that after four weeks storage at 23.9° C. (~room temperature), the viscosity should be >25 BKU (Brookfield Viscometer K Scale Unit; 1 BKU=~10,000 cps) so it will handle well and not run out of the tube or off of the brush. Four weeks is the estimated time from manufacture to delivery to store shelf, before the consumer would be able to purchase the product. The second benchmark is that, after twelve weeks storage at 40.6° C., the viscosity should be </=60 BKU, which approaches the threshold for ease in dispensing the paste from the tube. This accelerated test approximates two years storage on the store shelf.

The second criterion is fluoride compatibility. The industry standard is that the level of total soluble fluoride in a silica based toothpaste must not drop by more than 10% over a twelve week storage period at 40.6° C.

Accordingly, these tests were run on the MAP formulation in comparison to two samples of a standard sodium lauryl sulfate formulation. The SLS formulation preparation differed from the above described MAP formulation on only one respect, the point at which the surfactant, SLS or MAP, was added. In the usual SLS procedure, it would be added with the flavor, just before the final 5 min. mixing period. Since this was the first experiment with the MAP in a silica toothpaste formulation, and there was concern that the spray dried powder may not dissolve as readily in the formulation as the SLS, it was added before the silica to allow more mixing time to dissolve it. This did not appear to be necessary; subsequent experiments should confirm this. As shown in the following results, there was no essential difference between the MAP formulation and the SLS control formulations.

Table 2 summarizes the changes in viscosity of the three formulations over a twelve week period of storage at 23.9° and 40.6° C. All were within the required limits at four and twelve weeks.

TABLE 2

Viscosity Stability Study of Tooth Paste Formulations

| Tooth Paste Stability Test Formulations | | | | | Ave. Viscosity (BKU), 23.9 C. Storage @ | | | | Ave. Vis. (BKU), 40.6 C. Storage @ | | |
|---|---|---|---|---|---|---|---|---|---|---|---|
| NB Ref. | Batch # | Surfactant | Formula | Silica | Initial | 4 wks | 8 wks | 12 wks | 4 wks | 8 wks | 12 wks |
| R-0248 | 24.3 | SLS | BMG | T 73 | 23.2 | 31.3 | 34.6 | 32.8 | 38.2 | 41.1 | 39.8 |
| R-0248 | 25.3 | SLS | BMG | T 73 | 22.3 | 29.3 | 33.7 | 33.4 | 37.5 | 40.4 | 43.0 |
| R-0368 | 10-1 | MAP-L-200/K | BMG | T73 & T43 | 29.9 | 41.7 | 43.8 | 42.5 | 44.9 | 48.5 | 52.5 |
| | | | Tube # | | 1 | 5 | 7 | 9 | 23 | 25 | 27 |

Table 3 shows the changes in soluble fluoride concentration of the three formulations over the twelve week storage at 40.6° and a shorter, three week storage at 49° C. In this series also, the 40.6° storage resulted in only a small change in the soluble fluoride concentration. Again, all formulations passed.

TABLE 3

Soluble Fluoride Stability Tests

| Tooth Paste Formulations for Stability Testing | | | | | Soluble Fluoride Concentration, ppm | | | % F$^-$ Drop | % F$^-$ Drop |
|---|---|---|---|---|---|---|---|---|---|
| NB Ref. | Batch # | Surfactant | Formula | Silica | Initial | 3 wk@49 C. | 12 wk@40.6 C. | 3 wk@49 C. | 12 wk@40.6 C. |
| R-0248 | 24.3 | SLS | BMG | T73 | 1024 | 1029 | 990 | 0 | −3 |
| R-0248 | 25.3 | SLS | BMG | T73 | 1028 | 1033 | 1010 | 0 | −2 |
| R-0368 | 10-1 | MAP-L-200/K | BMG | T73 & T43 | 1030 | 995 | 995 | −4 | −4 |
| | | | Tube # | | 1 | 27 | | | |

The MAP formulations therefore do not cause or undergo any transformations which significantly affect either the viscosity or soluble fluoride concentration and are entirely suitable as a replacement for sodium lauryl sulfate in toothpaste formulations.

This formulation is meant to describe but not limit the invention. For instance, the total formulation in which the monoalkyl phosphate ester could be used, as well as the specific phosphate ester(s) which may be chosen, would depend upon the product. The various ingredients and proportions would be similar to those described in the references cited, incorporated herein by reference, and known to those skilled in the art as long as they did not significantly impair the anti-hypersensitivity performance of the soluble phosphate ester salt. The concentration of the phosphate ester salt would preferably range from 0.1-50 wt. %, or more and the specific phosphate ester salt composition would be selected, again, depending upon the method of application and the desired result.

What is claimed is:

1. A method for treating a hypersensitive tooth to reduce the sensitivity of the tooth, comprising:
   contacting the hypersensitive tooth with an oral care composition comprising,
   from 0.1 percent by weight to 50 percent by weight of water soluble phosphate ester salts as an agent effective to reduce tooth sensitivity,
   wherein all water soluble phosphate ester salts of the composition consist of one or more phosphate monoester salts according to structure (I) and one or more phosphate diester salts according to structure (II), wherein the molar ratio of the one or more phosphate monoester salts to the one or more phosphate diester salts is from 70:30 to 92:8,

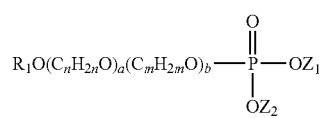
(I)

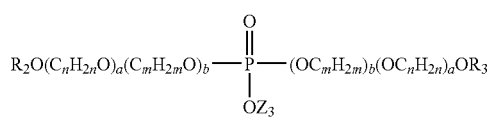
(II)

wherein the phosphate monoester salt according to structure (I) has a phosphate head group of structure (IA)

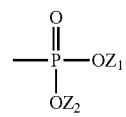
(IA)

and a hydrophobic tail of structure (IB)

$$R_1O(C_nH_{2n}O)_a(C_mH_{2m}O)_b— \quad \text{(IB); and}$$

wherein the phosphate diester salt according to structure (II) has a phosphate head group of structure (IIA)

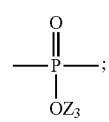
(IIA)

and hydrophobic tails of structures (IIB) and (IIC)

$$R_2O(C_nH_{2n}O)_a(C_mH_{2m}O)_b— \quad \text{(IIB),}$$

$$—(OC_mH_{2m})_b(OC_nC_{2n})_aOR_3 \quad \text{(IIC);}$$

wherein:
R$_1$, R$_2$, and R$_3$ are each individually linear or branched, saturated or unsaturated hydrocarbon groups of from 10 to 22 carbon atoms, n and m are each individually 2 to 4, a and b are each individually 0 to 20, one of Z$_1$ and Z$_2$ is alkali metal, ammonium, protonated alkyl amine, protonated alkanolamine, or protonated basic amino acid, and the other of Z$_1$ and Z$_2$ is hydrogen, alkali metal, ammonium, protonated alkyl amine, protonated alkanolamine, or protonated basic amino acid, and Z$_3$ is alkali metal, ammonium, protonated alkyl amine, protonated alkanolamine, or protonated basic amino acid;

at least one anti-caries agent selected from the group consisting of sodium fluoride and sodium monofluorophosphate wherein sodium trimetaphosphate is an optional additional anti-caries agent; and wherein the composition has an absence of calcium compounds;

wherein the composition has an absence of strontium salts;

wherein the phosphate head groups of the one or more water soluble phosphate monoester salts and the one or more water soluble phosphate diester salts anchor to calcium hydroxyapatite tooth structure of the hypersensitive tooth, the hydrophobic tails separate from the respective anchored phosphate head groups by hydrolysis, and the phosphate head groups after hydrolysis are fixed in place in the calcium hydroxyapatite tooth structure by reaction with calcium in saliva of an oral cavity in which the hypersensitive tooth is located.

2. The method of claim 1, wherein the oral care composition is a toothpaste or gel, a mouth wash, a chewing gum, a soluble oral care strip, or a lozenge.

3. The method of claim 2, wherein the oral care composition is a toothpaste or gel.

4. The method of claim 1, wherein
R$_1$, R$_2$, and R$_3$ are each individually linear or branched, saturated or unsaturated hydrocarbon groups of from 12 to 22 carbon atoms.

5. The method of claim 1,
wherein the oral care composition consists of:
said one or more water soluble phosphate monoester salts according to structure (I) and said one or more water soluble phosphate diester salts according to structure (II), wherein R$_1$, R$_2$, and R$_3$ are each individually linear or branched, saturated or unsaturated hydrocarbon groups of from 12 to 22 carbon atoms;

the anti-caries agent is at least one member selected from the group consisting of sodium fluoride and sodium monofluorophosphate, wherein sodium trimetaphosphate is an optional additional anti-caries agent; and at least one member selected from the group consisting of an abrasive polishing agent, flavor oil, sweetening agent, an anti-calculus agent, buffering agent, anti-staining compounds, anionic polymers, and alcohol;

wherein the abrasive polishing agent is at least one member selected from the group consisting of siliceous materials, sodium metaphosphate, insoluble sodium aluminosilicates, sodium bicarbonate, hydrated silica, colloidal silica, and fumed silica;

wherein the sweetening agent is at least one of saccharin and sorbitol;

wherein the anti-calculus agent is at least one member selected from water-soluble alkali metal salts of a polyphosphate;

wherein the buffering agent is at least one member selected from the group consisting of alkali metal orthophosphates, phosphoric acid, alkali metal glycerophosphates, tartrates, and citrates;

wherein the anti-staining compounds are selected from silicone polymers;

wherein the anionic polymers are selected from at least one member selected from the group consisting of polycarboxylates, polysulfonates, carboxylate and sulfonate copolymers, phosphonate polymers, and polyphosphates;

optionally a liquid selected from the group consisting of water and humectant, wherein said humectant is at least one member selected from the group consisting of glycerin, sorbitol, polyethylene glycols, polypropylene glycol, and hydrogenated partially hydrolyzed polysaccharides;

optionally a member selected from the group consisting of organic binder, inorganic thickener selected from the group consisting of silica and hydrated silica; nonionic surfactants, dye coloring agents, antibacterial agents, vitamin C, vitamin E, plant extracts, titanium dioxide, and tetrasodium pyrophosphate;

wherein the organic binder is selected from the group consisting of cellulose gum, glycerin, hydroxyethyl cellulose, hydroxypropyl cellulose, xanthan gum, Irish moss, and gum tragacanth;

wherein the antibacterial agents are at least one member of the group consisting of phenolics, salicylamides, and Triclosan.

6. The method of claim 1, wherein for all water soluble phosphate ester salts of the composition R$_1$, R$_2$, and R$_3$ are each individually linear or branched, saturated or unsaturated hydrocarbon groups of from 10 to 14 carbon atoms.

7. The method of claim 1, wherein for all water soluble phosphate ester salts of the composition R$_1$, R$_2$, and R$_3$ are each individually linear or branched, saturated or unsaturated hydrocarbon groups of from 12 to 14 carbon atoms.

8. The method of claim 7, wherein at least one said water soluble phosphate ester salt is potassium dodecyl phosphate.

9. The method of claim 7, wherein said phosphate ester salts each have a degree of ethoxylation of 0 to 4.

10. The method of claim 1, wherein said method also treats a tooth having lesions to enhance remineralization of the lesions during said step of contacting the tooth with said oral care composition that comprises at least one said water soluble phosphate ester salt, as an agent effective to enhance such remineralization.

11. The method of claim 10, wherein the oral care composition consists of:
the one or more water soluble phosphate monoester salts according to structure (I) and the one or more water soluble phosphate diester salts according to structure (II);

wherein R$_1$, R$_2$, and R$_3$ are each individually linear or branched, saturated or unsaturated hydrocarbon groups of from 12 to 14 carbon atoms, n and m are each individually 2 to 4, a and b are each individually 0 to 20, one of Z$_1$ and Z$_2$ is alkali metal, ammonium, protonated alkyl amine, protonated alkanolamine, or protonated basic amino acid, and the other of Z$_1$ and Z$_2$ is hydrogen, alkali metal, ammonium, protonated alkyl amine, protonated alkanolamine, or protonated basic amino acid, and $Z_3$ is alkali metal, ammonium, protonated alkyl amine, protonated alkanolamine, or protonated basic amino acid, the anti-caries agent is at least one member selected from the group consisting of sodium fluoride and sodium monofluorophosphate, wherein sodium trimetaphosphate is an optional additional anti-caries agent;

at least one member selected from the group consisting of an abrasive polishing agent, flavor oil, sweetening agent, an anti-calculus agent, buffering agent, anti-staining compounds, anionic polymers, and alcohol;

wherein the abrasive polishing agent is selected from at least one member of the group consisting of siliceous materials, sodium metaphosphate, insoluble sodium aluminosilicates, and sodium bicarbonate;

wherein the sweetening agent is at least one of saccharin and sorbitol;

wherein the anti-calculus agent is at least one member selected from water-soluble alkali metal salts of a polyphosphate;

wherein the buffering agent is at least one member selected from the group consisting of alkali metal orthophosphates, phosphoric acid, alkali metal glycerophosphates, tartrates, and citrates;

wherein the anti-staining compounds are selected from silicone polymers;

wherein the anionic polymers are selected from at least one member selected from the group consisting of polycarboxylates, polysulfonates, carboxylate and sulfonate copolymers, phosphonate polymers, and polyphosphates;

optionally a liquid selected from the group consisting of water and humectant, wherein said humectant is at least one member selected from the group consisting of glycerin, sorbitol, polyethylene glycols, polypropylene glycol, and hydrogenated partially hydrolyzed polysaccharides;

optionally a member selected from the group consisting of organic binder, inorganic thickener selected from the group consisting of silica and hydrated silica; nonionic surfactants, dye coloring agents, antibacterial agents, vitamin C, vitamin E, plant extracts, titanium dioxide, and tetrasodium pyrophosphate;

wherein the organic binder is selected from the group consisting of cellulose gum, glycerin, hydroxyethyl cellulose, hydroxypropyl cellulose, xanthan gum, Irish moss, and gum tragacanth;

wherein the antibacterial agents are at least one member of the group consisting of phenolics, salicylamides, and Triclosan.

12. The method of claim 11, wherein at least one said water soluble phosphate ester salt is potassium dodecyl phosphate.

13. The method of claim 11, wherein at least one said phosphate ester salt is alkyl ethoxylate phosphate ester salt having a degree of ethoxylation of 1 to 20.

14. The method of claim 1, wherein all the anti-caries agent of the composition is selected from at least one member of the group consisting of sodium fluoride and sodium monofluorophosphate.

15. The method of claim 1, wherein the water soluble phosphate ester salts consist of monoalkyl phosphate ester potassium salts and dialkyl phosphate ester potassium salts.

16. The method of claim 1, wherein at least one said phosphate ester salt is alkyl ethoxylate phosphate ester salt having a degree of ethoxylation of 1 to 20.

17. A method for treating a tooth having lesions to enhance remineralization of the lesions, comprising:

contacting the tooth with an oral care composition consisting essentially of from 0.1 percent by weight to 50 percent by weight of the water soluble phosphate ester salts as an agent effective to enhance such remineralization, wherein all water soluble phosphate ester salts of the composition consist of one or more phosphate monoester salts according to structure (I) and one or more phosphate diester salts according to structure (II), wherein the molar ratio of the one or more phosphate monoester salts to the one or more phosphate diester salts is from 70:30 to 92:8,

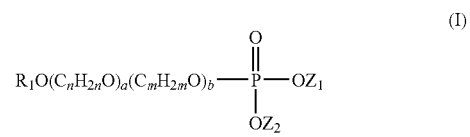

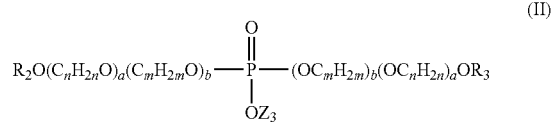

wherein the phosphate monoester salt according to structure (I) has a phosphate head group of structure (IA)

and a hydrophobic tail of structure (IB)

wherein the phosphate diester salt according to structure (II) has a phosphate head group of structure (IIA)

and hydrophobic tails of structures (IIB) and (IIC)

wherein:

$R_1$, $R_2$, and $R_3$ are each individually linear or branched, saturated or unsaturated hydrocarbon groups of from 10 to 22 carbon atoms, n and m are each individually 2 to 4, a and b are each individually 0 to 20, one of $Z_1$ and $Z_2$ is alkali metal, ammonium, protonated alkyl amine, protonated alkanolamine, or protonated basic amino acid, and the other of $Z_1$ and $Z_2$ is hydrogen, alkali metal, ammonium, protonated alkyl amine, protonated alkanolamine, or protonated basic amino acid, and $Z_3$ is alkali metal, ammonium, protonated alkyl amine, protonated alkanolamine, or protonated basic amino acid;

at least one anti-caries agent selected from the group consisting of sodium fluoride and sodium monofluorophosphate wherein sodium trimetaphosphate is an optional additional anti-caries agent; and wherein the composition has an absence of calcium compounds;

wherein the composition has an absence of strontium salts;

wherein the phosphate head groups of the one or more water soluble phosphate monoester salts and the one or more water soluble phosphate diester salts anchor to calcium hydroxyapatite tooth structure of the tooth having lesions, the hydrophobic tails separate from the respective anchored phosphate head groups by hydrolysis, and the phosphate head groups after hydrolysis are fixed in place in the calcium hydroxyapatite tooth structure by reaction with calcium in saliva of an oral cavity in which the tooth having lesions is located.

18. The method of claim 17, wherein the oral care composition consists of:

said one or more water soluble phosphate monoester salts according to structure (I) and said one or more water soluble phosphate diester salts according to structure (II), wherein $R_1$, $R_2$, and $R_3$ are each individually linear or branched, saturated or unsaturated hydrocarbon groups of from 12 to 22 carbon atoms;

the anti-caries agent is at least one member selected from the group consisting of sodium fluoride and sodium monofluorophosphate, wherein sodium trimetaphosphate is an optional additional anti-caries agent; and at least one member selected from the group consisting of an abrasive polishing agent, flavor oil, sweetening agent, an anti-calculus agent, buffering agent, anti-staining compounds, anionic polymers, and alcohol;

wherein the abrasive polishing agent is at least one member selected from the group consisting of siliceous materials, sodium metaphosphate, insoluble sodium aluminosilicates, sodium bicarbonate, hydrated silica, colloidal silica, and fumed silica;

wherein the sweetening agent is at least one of saccharin and sorbitol;

wherein the anti-calculus agent is at least one member selected from water-soluble alkali metal salts of a polyphosphate;

wherein the buffering agent is at least one member selected from the group consisting of alkali metal orthophosphates, phosphoric acid, alkali metal glycerophosphates, tartrates, and citrates;

wherein the anti-staining compounds are selected from silicone polymers;

wherein the anionic polymers are selected from at least one member selected from the group consisting of polycarboxylates, polysulfonates, carboxylate and sulfonate copolymers, phosphonate polymers, and polyphosphates;

optionally a liquid selected from the group consisting of water and humectant, wherein said humectant is at least one member selected from the group consisting of glycerin, sorbitol, polyethylene glycols, polypropylene glycol, and hydrogenated partially hydrolyzed polysaccharides;

optionally a member selected from the group consisting of organic binder, inorganic thickener selected from the group consisting of silica and hydrated silica; inorganic surfactants, dye coloring agents, antibacterial agents, vitamin C, vitamin E, plant extracts, titanium dioxide, and tetrasodium pyrophosphate;

wherein the organic binder is at least one member selected from the group consisting of cellulose gum, glycerin, hydroxyethyl cellulose, hydroxypropyl cellulose, xanthan gum, Irish moss, and gum tragacanth;

wherein the antibacterial agents are at least one member selected from the group consisting of phenolics, salicylamides, and Triclosan.

19. The method of claim 17, wherein the oral care composition is a toothpaste or gel, a mouth wash, a chewing gum, a soluble oral care strip, or a lozenge.

20. The method of claim 17, wherein the oral care composition is a toothpaste or gel.

21. The method of claim 17, wherein $R_1$, $R_2$, and $R_3$ are each individually linear or branched, saturated or unsaturated hydrocarbon groups of from 12 to 22 carbon atoms.

22. The method of claim 17, wherein for all water soluble phosphate ester salts of the composition $R_1$, $R_2$, and $R_3$ are each individually linear or branched, saturated or unsaturated hydrocarbon groups of from 10 to 14 carbon atoms.

23. The method of claim 17, wherein for all water soluble phosphate ester salts of the composition $R_1$, $R_2$, and $R_3$ are each individually linear or branched, saturated or unsaturated hydrocarbon groups of from 12 to 14 carbon atoms.

24. The method of claim 23, wherein at least one said water soluble phosphate ester salt is potassium dodecyl phosphate.

25. The method of claim 23, wherein said phosphate ester salts each have a degree of ethoxylation of 0 to 4.

26. The method of claim 17, wherein all the anti-caries agent of the composition is selected from at least one member of the group consisting of sodium fluoride and sodium monofluorophosphate.

27. The method of claim 17, wherein the water soluble phosphate ester salts consist of monoalkyl phosphate ester potassium salts and dialkyl phosphate ester potassium salts.

28. The method of claim 17, wherein at least one said phosphate ester salt is alkyl ethoxylate phosphate ester salt having a degree of ethoxylation of 1 to 20.

* * * * *